Figure 1:
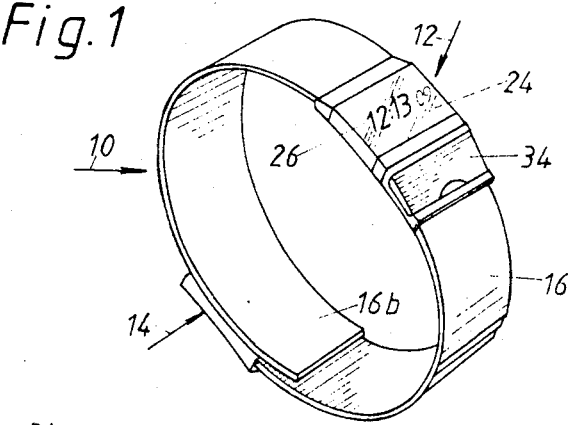

United States Patent [19]

Hirsch et al.

[11] Patent Number: 4,586,827
[45] Date of Patent: May 6, 1986

[54] INFORMATION SYSTEM

[76] Inventors: Hermann Hirsch, Hirschstrasse 5, A-9021 Klagenfurt (Karnten); Heinrich Pichler, Sailerackergasse 38/2, A-1190 Wien (Osterreich), Austria

[21] Appl. No.: 663,043

[22] Filed: Oct. 16, 1984

[30] Foreign Application Priority Data

Oct. 17, 1983 [AT] Austria ............................ 3698/83

[51] Int. Cl.⁴ ............................................. G04B 87/00
[52] U.S. Cl. ..................................... 368/282; 368/10; 455/351
[58] Field of Search .......... 368/88, 155, 156, 276–278, 368/281, 282, 291, 313, 10; 455/344, 351

[56] References Cited

U.S. PATENT DOCUMENTS

| | | | |
|---|---|---|---|
| 2,470,687 | 5/1949 | Cafrella et al. | 455/351 |
| 2,899,549 | 8/1959 | Potter | 455/351 |
| 4,023,344 | 5/1977 | Mukaiyama | 368/47 |
| 4,063,410 | 12/1977 | Welling | 368/10 |
| 4,070,649 | 1/1978 | Wright, Jr. et al. | 368/10 |
| 4,162,610 | 7/1979 | Levine | 368/10 |
| 4,427,303 | 1/1984 | Matthias | 368/282 |

Primary Examiner—Bernard Roskoski
Attorney, Agent, or Firm—Young & Thompson

[57] ABSTRACT

An information system is disclosed built up of at least two modules (14, 60, 62, 63, 64, 66, 67), which modules can be joined with each other by way of a band (16) attachable to a user wherein at least two mutually insulated electric connecting wires (18) are embedded. In at least one of the modules (14, 60, 62, 63, 64, 66, 67) a bushing (28) for the band (16) is provided, associated with a plurality of connecting pins electrically connected to the module, these pins being insertable in the insulating material (20) of the band (16) for electrical contacting.

1 Claim, 9 Drawing Figures

INFORMATION SYSTEM

The invention relates to an information system built up of at least two modules that can be joined with each other by way of a band attachable to a user wherein at least two mutually insulated electric connecting wires are embedded.

Electronic instruments, such as watches and also computers, have already been designed to be sufficiently compact and lightweight for being worn on one's wrist. Usually, these devices comprise a control circuit taking care of the time stability or the computing function. Another essential component of such a device is the information-yielding circuit providing the issuance of, for example, time and date or also other data of the control circuit in a form perceptible by the user, such as, for example, acoustically or visually. These circuits can exhibit liquid-crystal displays (called briefly LCD hereinbelow) or light-emitting diodes (called briefly LED hereinbelow) in the shape of alphanumeric symbols, but they can also be constituted by sound transducers, such as, for example, miniature loudspeakers. A further possibility also resides in providing, as the information-yielding circuit, an amplifier, optionally in conjunction with a receiver portion, wherein a small loudspeaker or headphone can be connected to the amplifier via a cable. A third essential component is represented by the energy supply, customarily a battery, supplying the electrical energy for the control circuit and display.

The information-yielding circuit, the battery, and the control circuit have heretofore been accommodated in a single module, since these components must be electrically interconnected. Such a watch or such a computer attached to a bracelet thus tends to be relatively bulky and top-heavy, especially if the housing is made of steel.

In order to reduce the size of such a module, it has also been proposed to arrange the control circuit and, respectively or, the battery in a separate module customarily worn on the other side of the bracelet. As a consequence, it was necessary to establish electrical connection through the bracelet between the various modules attached to the bracelet.

One suggestion for obtaining such a connection between the modules has been disclosed in U.S. Pat. No. 4,194,355. In this arrangement, electric connecting wires are embedded in the bracelet and provided with individual terminals at the end of the bracelet. These bracelet terminals form a plug fitting into electric connections of the display module. Although the connecting scheme proposed in this reference permits subdivision of the electric components into two modules, the connection between the wrist strap and the display module is complicated and therefore difficult and expensive in its manufacture.

Besides, the length of the wrist strap between the display module and the other module is fixed as soon as the plug has been attached to one end of the wrist strap in the factory. The length of the wrist strap between the display module and the separate electronic module thus cannot be readily adjusted to obtain adaptation to the various wrist sizes.

Furthermore, various line connectors have been suggested for connection to multiple-wire band cables. Thus, a line connector has been known from DAS 1,465,659 permitting connection of a conductor tape with a plug. In this system, the individual plugs are provided with spikes connected to the actual plug part, intended for insertion of a counterpart, by way of a component fashioned as a spring. These spikes penetrate into an angled end zone of the conductor tape and establish connection to the conductors. A slide movable by way of a lever is provided for effecting penetration of the spikes in this arrangement.

Besides, a plug has been proposed by British Patent No. 1,233,856 wherein the insulated end of a single conductor is clamped between spring-loaded hooks. In this arrangement, spikes are additionally provided which penetrate into the insulating-material casing of the conductors, but without coming into contact with the conductor, in order to retain this casing in case of tensile stress.

These conventional conductor connectors are burdened by the disadvantage, just as the plug for a conductor tape disclosed by European Patent No. 73 098, that the electrically conductive plug parts can be joined merely with the ends of the conductor tape so that these conventional solutions permit only connections at the end locations of the conductor tape.

It is an object of this invention to propose an improved information system of the type mentioned above wherein the modules can be connected to the band in a variable fashion; the band is to be such that it can be simply cut to a desired length. This is accomplished by providing that at least one of the modules has a bushing for the band, this bushing having an opening extending in parallel to the introduced band. A device conventionally carrying a plurality of connecting pins electrically connected to the module can be pressed into this opening, the connecting pins being insertable in the insulating material to establish electrical contact between the electronic module and the connecting wires of the band, which wires are connected to inputs and outputs of the associated module. Thereby it is also made possible to connect the individual parts of the information system to the band at any desired locations of the latter.

In a modification of this idea of the invention, it is also possible to arrange already prepared contact sites at the bracelet in (regular) intervals.

It is possible in this way to place the module at any desired location of the band, wherein the band can be altered in its length even after mounting the module, and the module can be changed in its arrangement on the band.

According to another feature of the invention, the provision can be made to arrange several modules on the band, at least one of these modules, for example the information-issuing module, being fixedly joined to the band and/or to the connecting wires embedded therein, and the others being provided with the device, operable by the user, which is equipped with the connecting pins electrically connected to the module for inserting these connecting pins at a desired location in the insulating material of the band. The fixed connection of one module or also a few modules to the band and/or to its connecting wires permits production of prefabricated information systems which, however, can even be further enlarged, if desired. Thus, an arbitrary enhancement and changing of the information system is readily possible by incorporation of additional modules or by the exchanging of modules. A further possibility for constructing an information system in accordance with the invention resides in providing all of the modules with the device, operable by the user, which is equipped with the connecting pins for inserting these connecting pins in the insulating material of the band at a desired location. It is made possible in this way to cut the band to any desired lengths and to stud it with any desired modules which latter can simply be anchored at any desired location in the band by means of the operating device, and can be connected to the connecting wires embedded in the band.

In this connection, it is advantageous if the device of the module for inserting the connecting pins comprises a flexible tongue at which the connecting pins are held, cooperating with a cam to insert the connecting pins in the insulating material. This results in a very simple structure and extensively avoids the risk of injury from the spikes during the insertion step.

In a preferred embodiment of the invention, the provision can be made that at least one of the connecting wires serves as an antenna, and one of the modules is constructed as a transmitter or receiver and is connected to the connecting wire provided as the antenna. In this arrangement, besides the information-issuing module, there are preferably also provided modules designed as an intelligent sensor which collects and processes data, as well as a module designed as a transmitter, if desired, which latter is optionally connected via the connecting wires with electrodes in contact with the user. In this way, it is possible to use such an information system as a permanent monitor of a patient's cardiac rhythm disturbances or the like, even if the patient goes for a walk. Also in this connection, the provision can be made that the sensor, in case of the occurrence of disturbances, triggers stimulus pulses in the transmitter to overcome the disturbances, these pulses being transmitted to the patient via electrodes.

Another possibility of using such an information system presents itself, for example, in the training of athletes.

Figure 2:
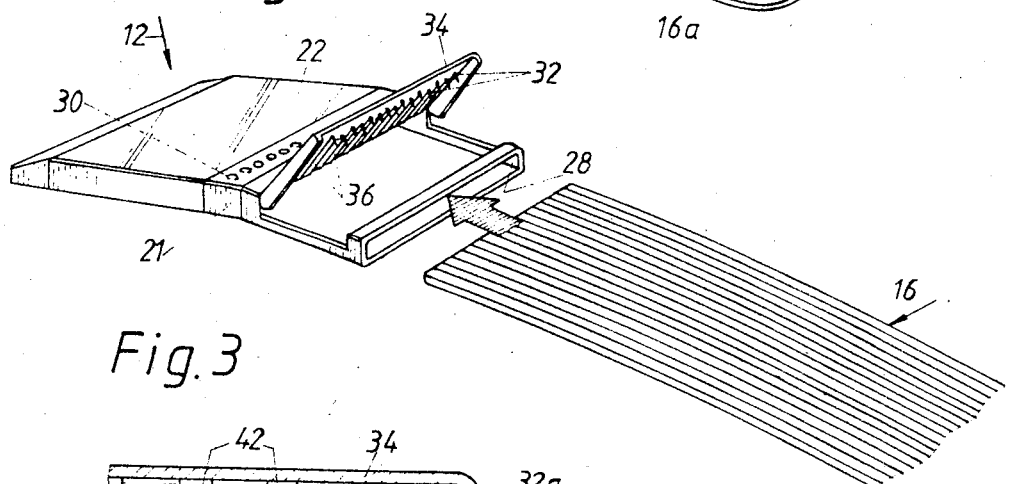
Figure 3:
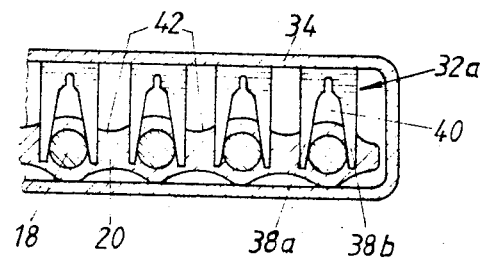
Figure 5:
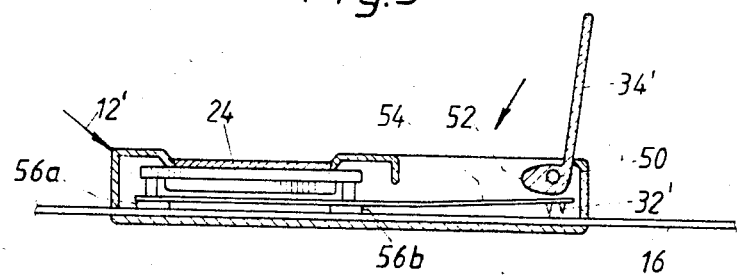
Figure 4:
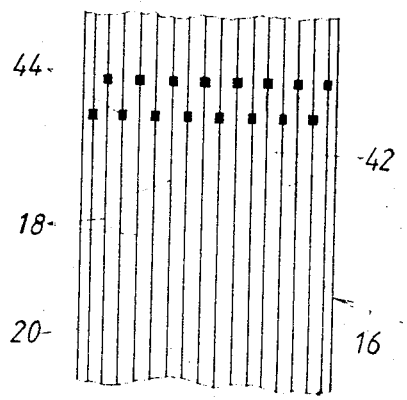
Figure 6:
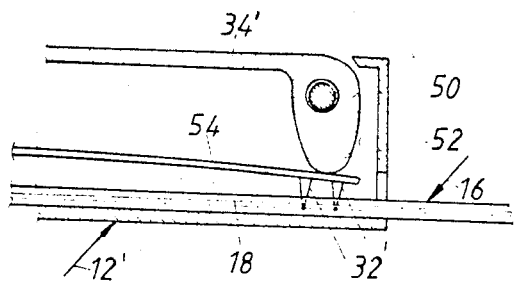
Figure 7:
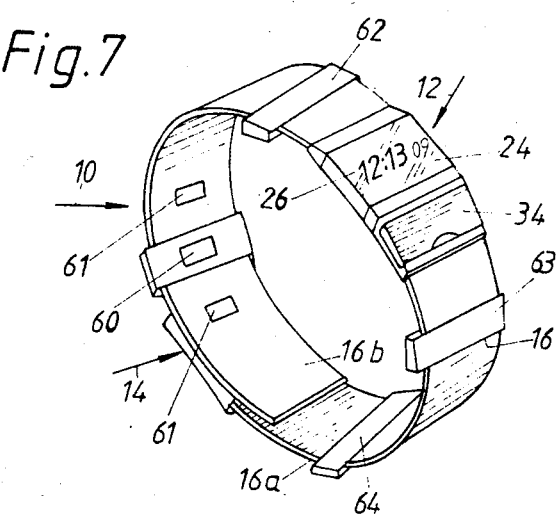
Figure 8:
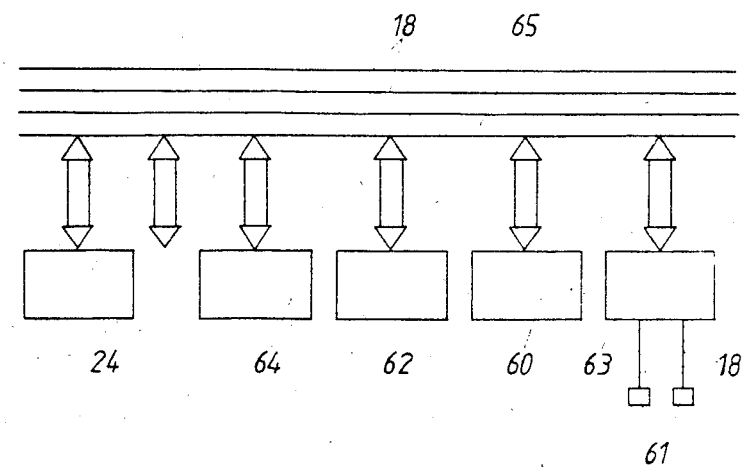
Figure 9:
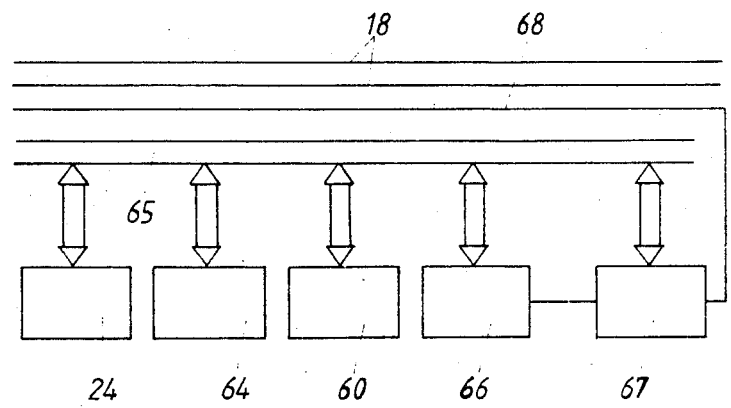

The invention will now be described in greater detail with reference to the drawings wherein:

FIG. 1 shows a view of an information system according to this invention,

FIG. 2 is a view of the information-issuing module according to FIG. 1, illustrating the insertion of the band in the information-issuing module, FIG. 3 is a cross section through the connection of the information-issuing module connecting pins with the connecting wires of the band, FIG. 4 shows a view of a portion of the band according to FIG. 1 on an enlarged scale revealing the arrangement of the connecting pins of the information-issuing module according to FIG. 1, FIG. 5 is a cross section through another embodiment of an information-issuing module according to FIG. 1, FIG. 6 is an information-issuing module cover according to FIG. 5 in the closed position, FIG. 7 is another embodiment of an information system according to the invention, FIG. 8 is a block circuit diagram of the information system of FIG. 7, and FIG. 9 is a block circuit diagram of another information system according to this invention.

As can be seen from FIG. 1, the information system of this invention, namely a wristwatch, is denoted by reference numeral 10. The wristwatch 10 comprises an information output module 12, constituted, for example, by an LCD display, and a separate electronic module 14, both modules being attached to the strap or bracelet 16 carried on the wrist. The wrist strap 16 has a plurality of connecting wires 18 arranged at equal spacings (FIG. 3) and embedded in a flexible insulating material 20. These connecting wires can also be arranged at spacings that are not equidistant, for example to ensure optimum contacting.

The information-issuing module 12 has a substantially rectangular housing 21 with a transparent cover 22. Underneath this transparent cover 22, a display circuit 24 is arranged which can indicate alphanumeric symbols 26. Although the illustrated embodiment shows a wristwatch, the invention is just as well applicable to other electronic devices carried on a strap, such as, for example, computers. Basically, the information system, as will be explained in connection with FIGS. 7-9, can be supplemented with a large number of different modules.

The separate electronic module 14 contains a timing circuit, not shown, which usually is designed as one or several integrated switching circuits. A battery, likewise not illustrated, serves for supplying energy to the electronic module 14 and to the display circuit 24; this battery is housed in the electronic module 14. The connecting wires 18 of the wrist band 16 are conventionally connected electrically to the outputs of the circuit of module 14. The information output module 12 can, however, be readily placed at any desired location along the wrist strap 16, as will be explained in greater detail below.

In order to position the information-issuing module 12 at the bracelet, the latter has a duct 28 (FIG. 2) extending over the entire length of the information output module 12; the bracelet can be threaded into this duct. Within the housing 21 of the information output module 12, a plurality of outputs of the display circuit 24 are arranged; these outputs are denoted by 30.

For connecting the outputs 30 of the information output module 12 to the connecting wires of the wrist strap 16, the module has a plurality of connecting pins 32 equipped with sharp spikes and located on a pivotable lid 34. Each connecting pin 32 is connected via a wire 36 to an output 30 of the display circuit 24. The connecting pins 32 are arranged in two rows and in coincidence with the connecting wires 18 of the bracelet where the latter is introduced into the duct 28. Once the display module 12 has been placed into the desired position at the wrist band, the lid 34 can be closed whereby the connecting pins 32 are driven into the wrist band.

FIG. 3 shows in detail the connection of the connecting pins 32 to the connecting wires 18 of the bracelet 16. A representative connecting pin is denoted by 32a and exhibits two tines 38a, 38b provided with sharp spikes which cut into the insulating material 20 of the wrist strap 16 when the lid 34 is closed. The tines 38a, 38b define a slot 40 into which engages the corresponding connecting wire 18a when the connecting pin is driven downwardly into the bracelet 16. The insulating material 20 has a lesser thickness between the connecting wires 18 to facilitate connection of the connecting pins 32 with the corresponding connecting wires 18.

FIG. 4 shows a pattern where the connecting pins 32, indicated by strokes 44, are in engagement with the connecting wires 18 of the bracelet.

In this way, the electrical connection is established between the connecting wires and the output terminals 30 of the display circuit 24. It is thus possible to arrange the display module 12 at any desired location on the bracelet 16; the display module need merely be shifted along the band into the desired position and can be fixed in place, and electrical contact can be established, by closing the lid 34 and by the accompanying penetration of the wrist strap. In this arrangement, the connecting pins 32 simultaneously serve for fixing the display module 12 on the bracelet 16 and prevent displacement of the display module 12 with respect to the bracelet 16.

The wristwatch 10 is then fully functional, the display module 12 being fully in contact with the separate electronic module 14 by way of the wrist strap 12, as can be seen from FIG. 1. The wristwatch 10 can be carried on the user's wrist by attaching the section 16a of the bracelet 16 to the outside of the free end 16b by means of a closure or clamping mechanism. It can be seen from FIG. 1 that the display module 12 can be attached to the wrist strap 16, since the display module is always placed on the side oppositely to the electronic module, independently of the wrist size of the user. This is usually desirable and imparts to the wristwatch a symmetrical appearance and a balanced feeling when it is worn. The excess length of the end 16b of the bracelet 16 can be simply cut off without impairing the electrical connection.

The display module 12, however, can also be shifted to some other location simply by lifting the lid 34, the connecting pins 32 separating from the wrist strap 16. After shifting the module 12 to a new position, the lid 34 can be closed again, whereby the connecting pins come again in contact with the connecting wires.

A modified embodiment of the information-issuing module 12 according to FIG. 1 is illustrated in FIG. 5 and denoted by 12'. The information output module 12' has a lid 34' articulated thereto, this lid being pivotably attached to the module by means of a stem 50. A cam 52 is provided at the articulated end of the lid 34' and is in contact with a flexible tongue 54. The tongue 53 has a plurality of connecting pins 32' designed similarly to the connecting pins 32 of FIG. 2. The tongue 54 is attached at its other end to two supports 56a and 56b of the component containing the integrated display circuit 24.

The connecting pins 32' are connected to the outputs of the display circuit 24 by means of connecting wires, not shown. The lid 34' acts as a lever to achieve an improved mechanical structure. When the lid 34' is being closed, the cam 52 presses on the tongue 54 and drives the connecting pins 32' into the wrist strap with the connecting wires 18 to establish electric contact as described above.

The wristwatch 10 is now completely ready for operation, the information-issuing module 12 being coupled to the separate electronic module 14 via the wrist strap 16, as illustrated in FIG. 1. The wristwatch 10 can now be worn on the wrist by the user by attaching the section 16a of the bracelet 16 to the outside of the free end 16b of the bracelet by means of a clamping closure. It can be seen from FIG. 1 that the information output module 12 can be fastened to the wrist strap 16 in such a way that the module will always be on the side oppositely to the electronic module 14, independently of the circumference of the wrist of the user. This is generally desirable and imparts to the wristwatch a symmetrical appearance and a comfortable and balanced wear feeling. The excess length of the wrist strap 16 in the zone of the end 16b can be cut off without impairment to the electric connection.

The information-issuing module 12 can also be shifted into a different position simply by lifting the lid 34 whereby the connecting pins 32 are disengaged from the bracelet 16. After displacing the module 12 into a new position, the lid 34 can be closed again to connect the connecting pins with the connecting wires.

The connecting pins 32a comprise portions 38a and 38b shaped so that they cut into the insulating material 20 of the bracelet once the lid 34 is closed. Portions 38a and 38b of the connecting pin define a slot 40 cooperating with the corresponding connecting wire 18 where the connecting pins 32a are driven into the wrist strap. The insulating material 20 exhibits zones 42 of reduced thickness between each of the connecting wires 18 in order to facilitate coupling of each connecting pin 32 with the corresponding connecting wire 18. FIG. 4 shows a pattern according to which the connecting pins 32, symbolized by parts 44, are in engagement with the connecting wires.

In this way, electrical connections are established between the connecting wires 18 and the outputs 30 of the display circuit 24. It can be seen therefrom that the information-yielding module 12 can be placed at any desired location along the wrist strap 16 by shifting this module to the desired site and closing the lid 34. By the closing of the lid, the wrist strap is penetrated and thereby contact is established. Furthermore, the connecting pins 32 serve for fixing the information-issuing module 12 on the bracelet 16 to prevent shifting of the module with respect to the bracelet.

A further development of the information system of this invention is schematically illustrated in FIG. 7. In this system, a sensor 60 is arranged on the wrist strap 16, this sensor responding, for example, to skin temperature or to pressure and being usable for instance, to measure the pulse frequency. The sensor 60 can be connected to a microprocessor to form an intelligent sensor, as presupposed in the associated block circuit diagram of FIG. 8. Also, two electrodes 61 are additionally provided on the wrist strap 16 according to FIG. 7; these electrodes are in contact with the user's skin and are likewise connected to the connecting wires embedded in the wrist strap by way of the aforementioned connecting pins, which latter are, however, no longer illustrated in FIG. 7.

The information system illustrated in FIGS. 7 and 8 comprises, besides the display circuit 24 pertaining to the information-yielding module 12, a timer 64, a computer 62, the intelligent sensor 60 mentioned above, and a control unit 63 to control the electrodes 64, all of which are designed as modules and are connected with one another by means of the connecting pins with the connecting lines in the wrist strap. For signal transmission between the individual modules 24 and 60–63, a bus 65 constituted by connecting wires is provided. This bus 65, intended for data and information transmission, can be designed as a one-bit bus, formed by two connecting wires, wherein the data transmission takes place sequentially according to a definite log, or as a multiple-bit bus, for example an eight-bit bus with a corresponding number of parallel connecting wires. However, it is more advantageous to provide a bus with a minimum number of wires to keep possible contacting problems down.

Besides the connecting wires required for the bus 65, additional contact wires are needed for the energy supply of the individual modules from the battery, not shown, and connecting wires for the connection of the control unit 63 with the associated electrodes 61; these wires are generally denoted by 18.

The information system according to FIGS. 7 and 8 is also suitable for the monitoring of patients suffering, for example, from cardiac arrhythmias; in case of a critical condition detected by the intelligent sensor 60, the control circuit 63 operates as a transmitter and transmits corresponding pulses to the electrodes 61 contributing toward elimination of such disturbances. It would also be possible in this way to communicate a silent alarm for any variables to the person wearing the system, i.e. an alarm which is not on an acoustic base but rather is transmitted to the person wearing the information system by way of stimulating currents.

FIG. 9 shows an embodiment modified as compared with FIGS. 7 and 8. In this embodiment, the calculator 62 as well as the electrodes 61 have been omitted, and the control unit 63 has been replaced by a control unit 66 operating a telemetering unit 67, which latter is connected to a connecting wire serving as an antenna 68. In this way, the data detected by the intelligent sensor 60 can be transmitted in a wireless fashion. Thus, in case of patients in intensive care but already ambulatory, data can be transmitted to a diagnostic computer without practically any bother to the patient who wears such an information system on the wrist, for example.

It is to be noted basically that the information output module need not absolutely include a display circuit but rather issuance of information is also possible acoustically by means of an appropriate signal transducer and a small loudspeaker or headphone.

By the structure of such an information system in accordance with this invention, it is not only possible to realize a modular subdivision of the hardware of the information system; rather, it is also possible, by plugging in additional firmware modules, to influence the capacity of the system on the software side. Thus, if the system is coupled with a small computer, the capacity of the computer can be modified in accordance with the particular usage in dependence on the 37 buttoned-on software modules" since, after all, the space on the band, especially if a wrist strap is involved, is limited.

Another structure of the information system of this invention would also be possible by mounting a radio receiver module, wherein the antenna necessary therefor can likewise be constituted by one of the connecting wires incorporated into the band, which latter can also be designed as a headband, for example.

We claim:

1. In an information system with several modules which are attached to a wrist strap, wherein mutually insulated electric connecting wires are embedded, and each module has feed-through means for accommodation of a wrist strap, a device operable by the user being provided in these feed-through means and being equipped with a plurality of connecting pins electrically connected to inputs and outputs of the module, connecting pins of this device being pluggable, for establishing electrical contact with the connecting wires, into insulating material of the wrist strap; the improvement in which at least one of the connecting wires (18) extends lengthwise of the strap and serves as an antenna, one of the modules (60) is a sensor which collects and processes data, and one of the modules (67) is a telemetering unit electrically connected to both the sensor and the connecting wire serving as the antenna, for transmitting electrically and in a wireless fashion information received from said sensor through said antenna to a remote station.

* * * * *